US012648843B2

(12) United States Patent
Hoffman

(10) Patent No.: US 12,648,843 B2
(45) Date of Patent: Jun. 9, 2026

(54) PROSTHETIC IMPLANTS HAVING SHELLS WITH FLEXIBLE NEEDLE STOP PATCHES MADE OF TWO OR MORE LAYERS OF TEXTILE MATERIAL

(71) Applicant: Mentor Worldwide LLC, Irvine, CA (US)

(72) Inventor: Michael Hoffman, Hillsborough, NJ (US)

(73) Assignee: Mentor Worldwide LLC, Irvine, CA (US)

( * ) Notice: Subject to any disclaimer, the term of this patent is extended or adjusted under 35 U.S.C. 154(b) by 833 days.

(21) Appl. No.: 17/864,507

(22) Filed: Jul. 14, 2022

(65) Prior Publication Data

US 2023/0059602 A1 Feb. 23, 2023

Related U.S. Application Data

(60) Provisional application No. 63/234,848, filed on Aug. 19, 2021.

(51) Int. Cl.
| | |
|---|---|
| *A61F 2/24* | (2006.01) |
| *A61B 90/00* | (2016.01) |
| *A61F 2/12* | (2006.01) |

(52) U.S. Cl.
CPC ................ *A61F 2/12* (2013.01); *A61B 90/02* (2016.02); *A61F 2250/0003* (2013.01)

(58) Field of Classification Search
CPC ................ A61F 2/12; A61F 2250/0003; A61F 2210/0076; A61F 2250/0069; A61B 90/02
See application file for complete search history.

(56) References Cited

U.S. PATENT DOCUMENTS

| 4,190,040 A | 2/1980 | Schulte |
|---|---|---|
| 4,455,691 A | 6/1984 | Van Aken Redinger et al. |
| | (Continued) | |

FOREIGN PATENT DOCUMENTS

| CA | 2931028 | 5/2014 |
|---|---|---|
| EP | 2919709 | 7/2019 |
| | (Continued) | |

OTHER PUBLICATIONS

International Search Report issued in corresponding International Application No. PCT/IB2022/056847, mailed on Nov. 16, 2022, 5 pages.

(Continued)

*Primary Examiner* — Suzette J Gherbi

(74) *Attorney, Agent, or Firm* — TROUTMAN PEPPER LOCKE LLP

(57) ABSTRACT

A prosthetic implant, such as a tissue expander, includes a silicone shell having an anterior wall and a posterior wall, and a needle stop patch secured over an inner surface of the posterior wall of the silicone shell. The needle stop patch has two or more layers of a textile material that are stacked atop one another. The textile material is flexible and includes woven threads or fiber. A bonding material bonds together the two or more layers of the textile material that are stacked atop one another. The outer edges of the respective layers are feathered for minimizing step effects between adjacent ones of the layers. A self-sealing membrane covers the anterior wall of the silicone shell. The dernier level of the textile layers increases between top and bottom layers for progressively increasing resistance tom a needle passing through the needle stop patch.

23 Claims, 13 Drawing Sheets

(56) References Cited

U.S. PATENT DOCUMENTS

| | | | |
|---|---|---|---|
| 4,472,226 | A | 9/1984 | Redinger et al. |
| 4,908,029 | A | 3/1990 | Bark et al. |
| 4,960,425 | A | 10/1990 | Yan et al. |
| 5,022,942 | A | 6/1991 | Yan et al. |
| 5,049,393 | A | 9/1991 | Noon et al. |
| 5,066,303 | A | 11/1991 | Bark et al. |
| 5,133,753 | A | 7/1992 | Bark et al. |
| 5,240,773 | A * | 8/1993 | Dunn ........................ A61F 5/01 |
| | | | 525/317 |
| 5,314,653 | A | 5/1994 | Haralambopoulos |
| 6,428,571 | B1 | 8/2002 | Lentz et al. |
| 6,440,118 | B2 | 8/2002 | Burr et al. |
| 6,743,254 | B2 | 6/2004 | Guest et al. |
| 7,767,874 | B2 * | 8/2010 | Kellogg ............ A61F 13/01038 |
| | | | 442/30 |
| 8,070,828 | B2 | 12/2011 | Shannon |
| 8,255,035 | B2 | 8/2012 | Cao et al. |
| 8,690,943 | B2 | 4/2014 | Schuessler |
| 8,870,952 | B2 | 10/2014 | Holland et al. |
| 8,981,621 | B2 | 3/2015 | Pelrine et al. |
| 9,351,824 | B2 | 5/2016 | Renke |
| 9,463,087 | B2 | 10/2016 | Hristov et al. |
| 9,700,404 | B2 | 7/2017 | Martin et al. |
| 10,010,395 | B2 | 7/2018 | Puckett et al. |
| 10,070,951 | B2 | 9/2018 | Renke |
| 10,391,199 | B2 | 8/2019 | Liu et al. |
| 10,765,506 | B2 | 9/2020 | Chitre et al. |
| 10,820,984 | B2 | 11/2020 | Renke |
| 11,202,853 | B2 | 12/2021 | Liu et al. |
| 12,201,773 | B1 * | 1/2025 | Luo ................... A61M 16/0683 |
| 2002/0106959 | A1 * | 8/2002 | Huffines ............ A61F 13/51478 |
| | | | 442/381 |
| 2003/0149481 | A1 | 8/2003 | Guest et al. |
| 2005/0131325 | A1 | 6/2005 | Chen et al. |
| 2009/0030515 | A1 | 1/2009 | Schuessler et al. |
| 2009/0036794 | A1 | 2/2009 | Stubhaug et al. |
| 2010/0049316 | A1 | 2/2010 | Schuessler |
| 2011/0270391 | A1 * | 11/2011 | Chitre .................... A61B 90/02 |
| | | | 623/8 |
| 2011/0276133 | A1 | 11/2011 | Liu et al. |
| 2011/0288639 | A1 | 11/2011 | Trilokekar |
| 2011/0306827 | A1 | 12/2011 | Chitre |
| 2013/0023987 | A1 | 1/2013 | Liu et al. |
| 2013/0131799 | A1 | 5/2013 | Schuessler |
| 2014/0088703 | A1 | 3/2014 | Schuessler |
| 2014/0094662 | A1 | 4/2014 | Van Epps et al. |
| 2016/0022866 | A1 | 1/2016 | Liu et al. |
| 2016/0074152 | A1 | 3/2016 | Chitre et al. |
| 2016/0081783 | A1 | 3/2016 | Puckett et al. |
| 2017/0165908 | A1 * | 6/2017 | Pattinson ............... B33Y 80/00 |
| 2019/0000608 | A1 | 1/2019 | Renke |
| 2020/0038550 | A1 | 2/2020 | Liu et al. |
| 2022/0280281 | A1 | 9/2022 | Hoffman et al. |
| 2023/0285974 | A1 | 9/2023 | Siu et al. |
| 2025/0114187 | A1 * | 4/2025 | Chitre .................... A61B 90/02 |

FOREIGN PATENT DOCUMENTS

| | | |
|---|---|---|
| WO | 2014078498 | 5/2014 |
| WO | 2017184962 | 10/2017 |
| WO | 2020055740 | 3/2020 |
| WO | 2023021345 A1 | 2/2023 |

OTHER PUBLICATIONS

International Search Report issued in corresponding International Application No. PCT/IB2022/051692, mailed on May 30, 2022, 5 pages.

* cited by examiner

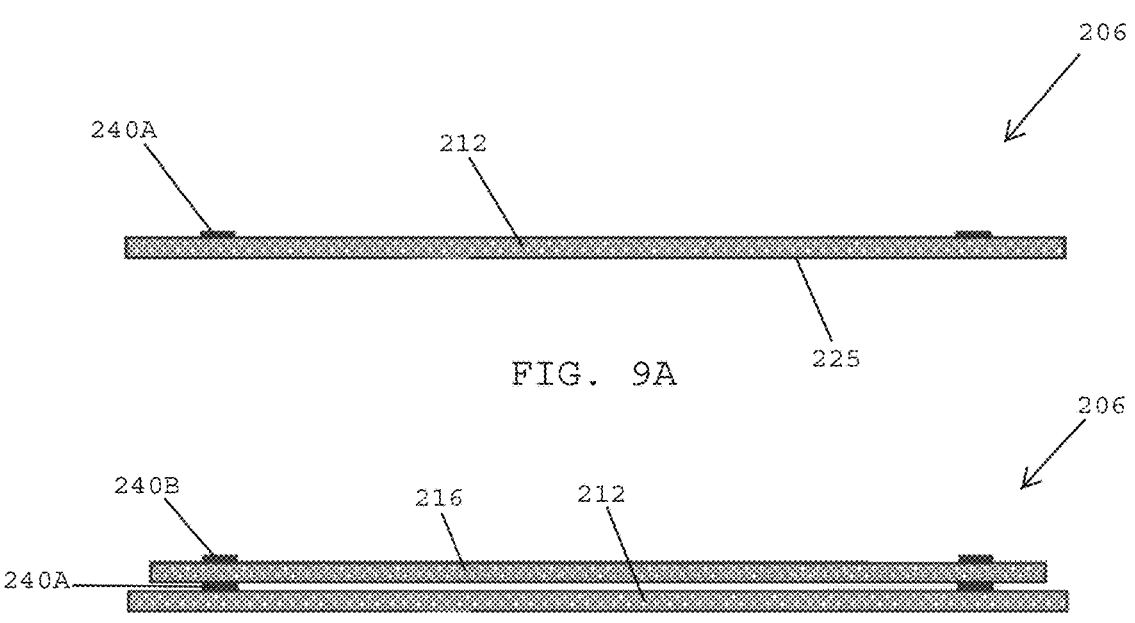
FIG. 9A
FIG. 9B
FIG. 9C
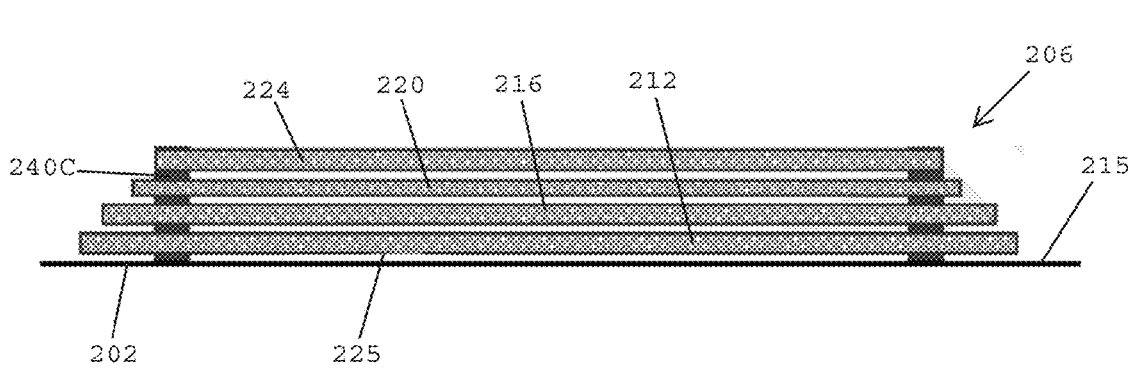
FIG. 9D

PROSTHETIC IMPLANTS HAVING SHELLS WITH FLEXIBLE NEEDLE STOP PATCHES MADE OF TWO OR MORE LAYERS OF TEXTILE MATERIAL

CROSS-REFERENCE TO RELATED APPLICATIONS

The present patent application claims benefit of U.S. Provisional Application Ser. No. 63/234,848, filed on Aug. 19, 2022, the disclosure of which is hereby incorporated by reference herein.

BACKGROUND OF THE INVENTION

Field of the Invention

The present patent application is generally related to implantable prosthetic implants such as breast implants and tissue expanders and is more specifically related to needle stops and needle guards that are incorporated into the shells of tissue expanders.

Description of the Related Art

Tissue expanders are devices that are implanted beneath the skin or muscle and then gradually inflated with fluid to stretch the overlying tissue. Tissue expanders are typically used to either create a pocket for receiving a permanent prosthesis, or to generate an increased skin surface area in anticipation of the new skin being utilized for grafting or reconstruction.

Tissue expanders are typically formed of a silicone polymer shell. After implantation, a fluid, such as saline, is periodically injected into the tissue expander to enlarge it over time. Between injections, the surrounding skin is permitted to stretch and grow to create the increased skin surface and the increased tissue pocket for receipt of a permanent implant.

A tissue expander can be provided with an injection port (e.g., a port comprising a septum) that can be pierced with a hypodermic needle for introducing fluid into the expander. It can be difficult, however, to accurately locate the injection port through the overlying tissue. If the injection port is missed and the needle punctures the shell of the tissue expander, the expander can leak. Most often, this requires the expander to be removed and replaced. This problem can be addressed by providing an injection port that is remote from the tissue expander but that is in fluid communication with the expander. Such systems are described in U.S. Pat. No. 4,190,040.

Other solutions include eliminating the need for an injection site altogether by forming the expander with a self-sealing shell that can be pierced with a hypodermic needle at any point for the purpose of adding fluid to the shell. For example, U.S. Pat. No. 5,066,303 discloses a tissue expander formed using a self-sealing shell material that reportedly can be safely pierced in any location.

U.S. Pat. No. 6,743,254 to Guest et al., assigned to Mentor Corporation, the disclosure of which is hereby incorporate by reference herein, teaches a tissue expander that contains a self-sealing area that surrounds an injection port. The self-sealing area reduces the risk of causing a leak in the expander when a hypodermic needle that is used to fill the expander misses the injection port, thereby reducing the frequency with which expanders require removal due to leakage caused by inadvertent punctures.

Tissue expanders may incorporate flexible needle stops that enable the tissue expander to be folded for insertion into a patient. For example, U.S. Pat. No. 4,908,029 to Bark et al. discloses a flexible needle stop that includes a normally unfolded an impenetrable needle barrier formed of a flexible foldable material. The flexible foldable material can be a single layer sheet material, a wire mesh material and/or one or more layers of scale-like components arranged side by side. The scale-like components are physically unconnected and of a size that permits flexion of the needle stop. The flexible needle stop can include a bead-like periphery, which affords the needle stop with a resilient memory and helps restore the needle stop member to its normally unfolded condition after a folding restraint is removed. The needle stop can be freely disposed within a fill chamber of a tissue expander, attached to an inner surface of the fill chamber, or incorporated in the shell wall of a tissue expander.

U.S. Patent Application Publication No. 2016/0074152 to Chitre et al. discloses a method of making a needle guard for an inflatable prosthesis suitable for implantation in a mammal. The method includes the steps of providing a first layer of puncture resistant members, for example, elongated slats, providing a second layer of puncture resistant members such that the second layer of members overlies and is offset from the first layer of members, and molding or otherwise applying a flexible material to the first layer of members and the second layer of slats to form a device useful as a needle guard for an inflatable prosthesis. The step of applying or molding includes coupling the members to (e.g., encasing the members within) the flexible material.

Materials are often evaluated to determine their suitability for being used to make needle stops. FIGS. 1 and 2 show a prior art system 50 that is configured for testing materials that are used to make needle stops for prosthetic devices. The system 50 tests the materials to ensure that the needles used to fill prosthetic implants will fail (e.g., by bending) before the material utilized to make the needle stop fails. The testing system 50 includes an Instron machine 52 that holds a needle 54. The Intron machine 52 moves the needle 54 up and down along a vertical axis $A_1$ so that a sharpened needle tip at a lower end of the needle engages the materials that are being evaluated.

The testing system 50 includes a fixture plate 56 that holds the material 58 that is being evaluated. Pursuant to standard ASTM 1441-03, the needle 54 must fail against the material 58 before the material fails. According to the ASTM 1441-03 standard, during testing, a 21-gauge needle having a length of 1.5 inches is utilized. The Instron machine 52 applies a downward force on the needle 54 against the material 58, and the 21-gauge needle breaks at approximately 6.5 pounds per foot. Therefore, for the material 58 to satisfy the ASTM 1441-03 standards and be fit to serve as an effective needle stop barrier, the material 58 must prevent needle penetration for forces of greater than 6.5 pounds per foot. If the needle 54 penetrates through the material 58 before the needle fails (e.g., bends), then the material 58 has not met the ASTM 1441-03 standard and cannot be used to make an effective needle guard.

Referring to FIG. 3, when certain materials (e.g., metal sheets) are used to make needle stops, the sharpened needle tip 60 of the needle 54 (FIG. 2) may become damaged. In FIG. 3, the sharpened needle tip 60 is damaged and is bent into a fishhook shaped configuration. In addition, lateral surfaces within a tapered region 62 of the needle 54 are also damaged.

In prosthetic implants with self-sealing shells, needles are passed through the shell and advanced into an interior chamber of the shell to fill the prosthetic implant with a filler material (e.g., gel; saline solution). If the prosthetic implant has a conventional needle guard, the sharpened tip of the needle may be damaged (e.g., bent into a fishhook shape) if it is pressed against the needle guard. When the damaged needle is later withdrawn from the shell (e.g., after the shell is filled), the damaged tip of the needle may tear or puncture the shell, which may cause catastrophic damage to the shell, including shells meant to self-seal after needle withdrawal.

Referring to FIG. 4, when the damaged needle 54 shown in FIG. 3 is withdrawn from the shell 64 of a prosthetic device, the fishhook-shaped tip 60 is likely to for a tear 66 or puncture in the shell 64. The tear 66, created by the fishhook-shaped tip 60 of the damaged needle 54 will allow the filling material 68 that fills the inside of the shell 64 to flow out of the tear 66. Thus, catastrophic damage to the shell 64 of a prosthetic device may result when a damaged needle is withdrawn from a shell after filling the shell with a gel or a saline solution.

In view of the above deficiencies in the prior art, there is a need for providing a prosthetic implant with a needle stop that can resist greater than 6.5 pounds of force (in the case of a 21-G needle), while minimizing needle tip damage that could result in a failure of the shell of an implant.

SUMMARY OF THE INVENTION

Conventional breast tissue expanders typically incorporate an integrated injection port. Though the injection port provides an important functionality, namely the ability to inflate and deflate of the tissue expander via percutaneous puncture with a needle, it also adds bulk to the tissue expander, resulting in reduced flexibility when folding and inserting the expander into the breast pocket and potentially increased patient discomfort and palpability.

In one embodiment, a construction for a needle stop patch is disclosed that minimizes needle tip damage, which may result in shell tearing and damage that normally would not be prevented from self-sealing shell constructs. The prior art includes numerous disclosures of self-sealing elastomeric shell membranes, which address self-sealing when penetrated with normal needles but do not account for the withdrawal of a potentially damaged needle tip. The needle stop patch disclosed herein improves upon the prior art by reducing the potential of needle deformation, which may result in shell tearing and leaks.

In one embodiment, the needle stop patch provides an impenetrable posterior backing that provides numerous improvements over the prior art.

First, the needle stop patch disclosed herein is impenetrable to needle puncture up to a specified gauge size (i.e., the needle must fail without penetrating through the needle stop patch).

In one embodiment, the needle stop patch is flexible (i.e., low bending stiffness) so that it can be easily folded and inserted into a breast pocket.

In one embodiment, the needle stop patch has a sufficient thickness and has an open communication to the internal lumen of the shell so that when a needle is pressed against the needle stop patch, the needle hole is not occluded, and the expander can be inflated even if it is in an initially collapsed/empty state.

In one embodiment, the needle stop patch is constructed so that it stops the needle from penetrating while minimizing the damage to the needle tip. In traditional expander injection ports, when needles are pressed against the port stop, it is possible to cause the tip of the needle to be damaged into a "fish-hook" shape. This is typically mitigated with the use of a more flexible polymeric dampening layer on the stop, but tip damage is still possible given the rigid nature of the stop. The needle stop patch disclosed herein is made of multiple layers of a textile material. One or more of the layers may include elastomeric sheeting. The layers of the textile material result in large frictional forces on the needle so that the penetration force is broadly distributed on the needle rather than localizing at the tip.

As used herein, the term textile material means a flexible material made by creating an interlocking network of threads, which are produced by spinning raw fibers from either natural or synthetic sources into long and twisted lengths. Textiles may be formed by weaving, knitting, crocheting, knotting, tatting, felting, bonding or braiding the threads together.

In one embodiment, a self-sealing shell membrane self-seals when punctured with a needle up to a specified gauge size. In one embodiment, a self-sealing tissue expander is disclosed that eliminates the need for a port by incorporating a self-sealing shell.

In one embodiment, a prosthetic implant, such as a tissue expander, preferably includes a silicone shell having an anterior wall and a posterior wall, and a needle stop patch secured over an inner surface of the posterior wall of the silicone shell.

In one embodiment, the needle stop patch may include two or more layers of a textile material (e.g., 4-10 layers) that are stacked atop one another to form a multi-layer structure.

In one embodiment, a bonding material is used for bonding together the two or more layers of the textile material that are stacked atop one another.

In one embodiment, the textile material may include natural or synthetic threads or fibers that are woven together to form a layer for a needle stop patch.

In one embodiment, the bonding material (e.g., curable silicone material) preferably passes through the two or more layers of the textile material for bonding the layers together.

In one embodiment, each of the two or more layers has an outer edge that defines an outer perimeter. In one embodiment, only the outer perimeters of the two or more layers are bonded together.

In one embodiment, the layers have different sizes. In one embodiment, the outer perimeter of a top layer of the two or more layers defines a first area and the outer perimeter of a bottom layer of the two or more layers defines a second area that is larger than the first area of the top layer.

In one embodiment, the outer perimeter of an intermediate layer of the two or more layers, which is between the top layer and the bottom layer, defines an intermediate area that is larger than the first area of the top layer and smaller than the second area of the bottom layer.

In one embodiment, the respective outer edges of the two or more layers are feathered for minimizing step effects between adjacent ones of the two or more layers.

In one embodiment, the bonding material may secure the needle stop patch to the posterior wall of the silicone shell.

In one embodiment, wherein each of the two or more layers of the textile material has a circular or oval shape.

In one embodiment, the bonding material has a ring shape that matches the circular or oval shape of each of the two or more layers of the textile material.

In one embodiment, at least one of the two or more layers of the textile material is laminated in elastomeric sheeting.

In one embodiment, the anterior wall of the silicone shell may include a self-sealing membrane.

In one embodiment, the self-sealing membrane may include a three-layer construction having a middle layer of an elastomeric material having first and second major surfaces, a first outer layer of an elastomeric material overlying the first major surface of the middle layer, and a second outer layer of an elastomeric material overlying the second major surface of the middle layer, whereby the middle layer of the elastomeric material holds the first and second outer layers of the elastomeric material in contraction.

In one embodiment, each layer of the two or more layers of the textile material has a top surface, a bottom surface and a plurality of holes that extend from the top surface to the bottom surface.

In one embodiment, a needle may be used for filling the silicone shell with a fluid (e.g., a gel; a saline solution). In one embodiment the needle has a cross-sectional area and a total combined area of the plurality of the holes for each layer is preferably greater than the cross-sectional area of the needle.

In one embodiment, the denier count of the two or more layers of the needle stop patch progressively increases from a top layer to a bottom layer of the patch for providing the needle stop patch with a progressively increasing resistance level from the top layer to the bottom layer.

In one embodiment, a top layer of the two or more layers of the textile material has a first denier count and a bottom layer of the two or more layers of the textile material has a second denier count that is greater than the first denier count of the top layer.

In one embodiment, a prosthetic implant preferably includes a silicone shell having an anterior wall and a posterior wall, and a needle stop patch secured over an inner surface of the posterior wall of the silicone shell.

In one embodiment, the needle stop patch preferably includes a plurality of layers of a textile material that are stacked atop one another, and a bonding material for joining together the plurality of layers of the textile material that are stacked atop of another.

In one embodiment, a self-sealing membrane may be integrated into the anterior wall of the silicone shell.

In one embodiment, the self-sealing membrane desirably includes a middle layer of an elastomeric material having first and second major surfaces, a first outer layer of an elastomeric material overlying the first major surface of the middle layer, and a second outer layer of an elastomeric material overlying the second major surface of the middle layer, whereby the middle layer of the elastomeric material holds the first and second outer layers of the elastomeric material in contraction.

In one embodiment, an outer surface of the first outer layer of the elastomeric material is secured to an inner surface of the anterior wall of the silicone shell.

In one embodiment, a top layer of the plurality of the layers has an outer edge defining a first area and a bottom layer of the plurality of layers has an outer edge defining a second area that is larger than the first area of the top layer.

In one embodiment, an intermediate layer of the plurality of layers, which is located between the top layer and the bottom layer, preferably has an outer edge that defines an intermediate area that is larger than the first area of the top layer and smaller than the second area of the bottom layer.

In one embodiment, the respective outer edges of each of the plurality of layers are desirably feathered for minimizing step effects between adjacent ones of the plurality of layers.

In one embodiment, each layer of the plurality of layers of the textile material has a top surface, a bottom surface and a plurality of holes that extend from the top surface to the bottom surface.

In one embodiment, a needle may be used for filling the silicone shell with a fluid. In one embodiment, the needle has a cross-sectional area and a total combined area of the plurality of holes for each layer is preferably greater than the cross-sectional area of the needle.

In one embodiment, the denier count of each layer of a needle stop patch progressively increases from the top layer to the bottom layer for progressively increasing resistance levels within the needle stop patch.

In one embodiment, the top layer of the plurality of layers of the textile material has a first denier count and the bottom layer of the plurality of layers of the textile material has a second denier count that is greater than the first denier count of the top layer.

In one embodiment, a method of making a multi-layer needle stop patch for a silicone shell preferably includes obtaining a first layer of a textile material, the first layer having an outer edge that defines a first area for the first layer and centering a second layer of a textile material over the first layer, the second layer having an outer edge that defines a second area for the second layer that is less than the first area for the first layer.

In one embodiment, the method preferably includes centering a third layer of a textile material over the second layer, the third layer having an outer edge that defines a third area for the third layer that is less than the second area for the second layer.

In one embodiment, the method preferably includes centering a fourth layer of a textile material over the third layer, the fourth layer having an outer edge that defines a fourth area for the fourth layer that is less than the third area for the third layer.

In one embodiment, the method includes bonding the respective outer edges of the first, second, third and fourth layers together to form a multi-layer stack.

In one embodiment, the respective outer edges of the layers are feathered for reducing step effects between the first, second, third and fourth layers.

In one embodiment, the method includes providing a silicone shell having an anterior wall and a posterior wall and securing the first layer of the multi-layer needle stop patch to an inner surface of the posterior wall of the silicone shell.

In one embodiment, each layer may include a plurality of holes extending from a top surface to a bottom surface thereof.

In one embodiment, the first layer of a textile material has a first denier count, the second layer of a textile material has a second denier count that is less than the first denier count, the third layer of a textile material has a third denier count that is less than the second denier count, and the fourth layer of a textile material has a fourth denier count that is less than the third denier count.

In one embodiment, at least one of the layers of a textile material is laminated in elastomeric sheeting.

These and other preferred embodiments of the present patent application will be described in more detail herein.

BRIEF DESCRIPTION OF THE DRAWINGS

FIG. 9A shows a first stage of a method of making a needle stop patch, in accordance with one embodiment of the present application.

FIG. 9B shows a second stage of a method of making a needle stop patch, in accordance with one embodiment of the present patent application.

FIG. 9C shows a third stage of a method of making a needle stop patch, in accordance with one embodiment of the present patent application.

FIG. 9D shows a fourth stage of a method of making a needle stop patch, in accordance with one embodiment of the present patent application.

DETAILED DESCRIPTION OF PREFERRED EMBODIMENTS

Figure 1:
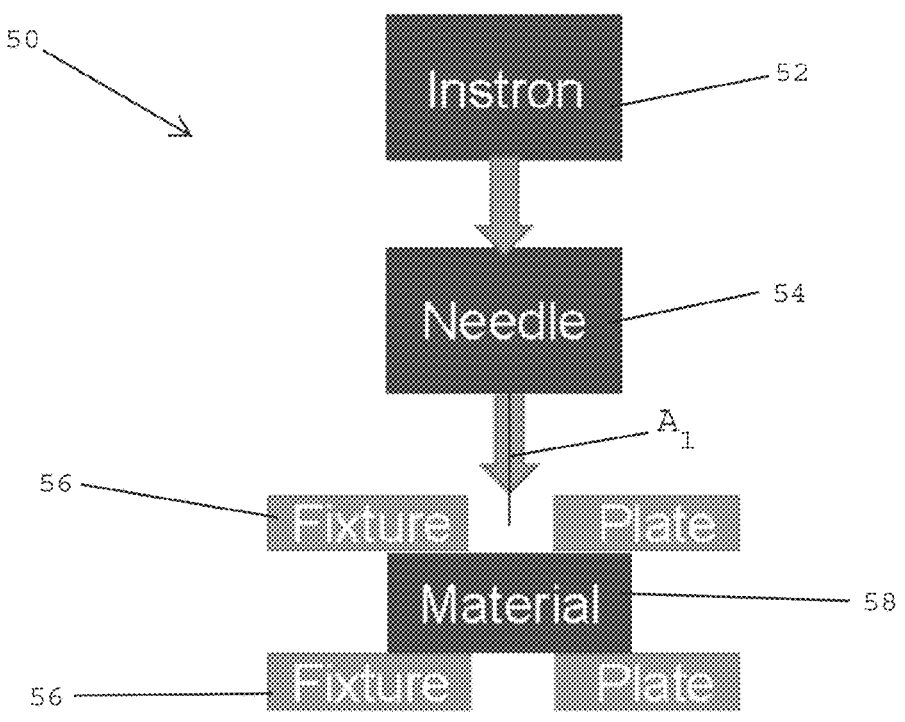
FIG. 1 is a schematic view of a prior art system used for testing a needle stop.
Figure 2:
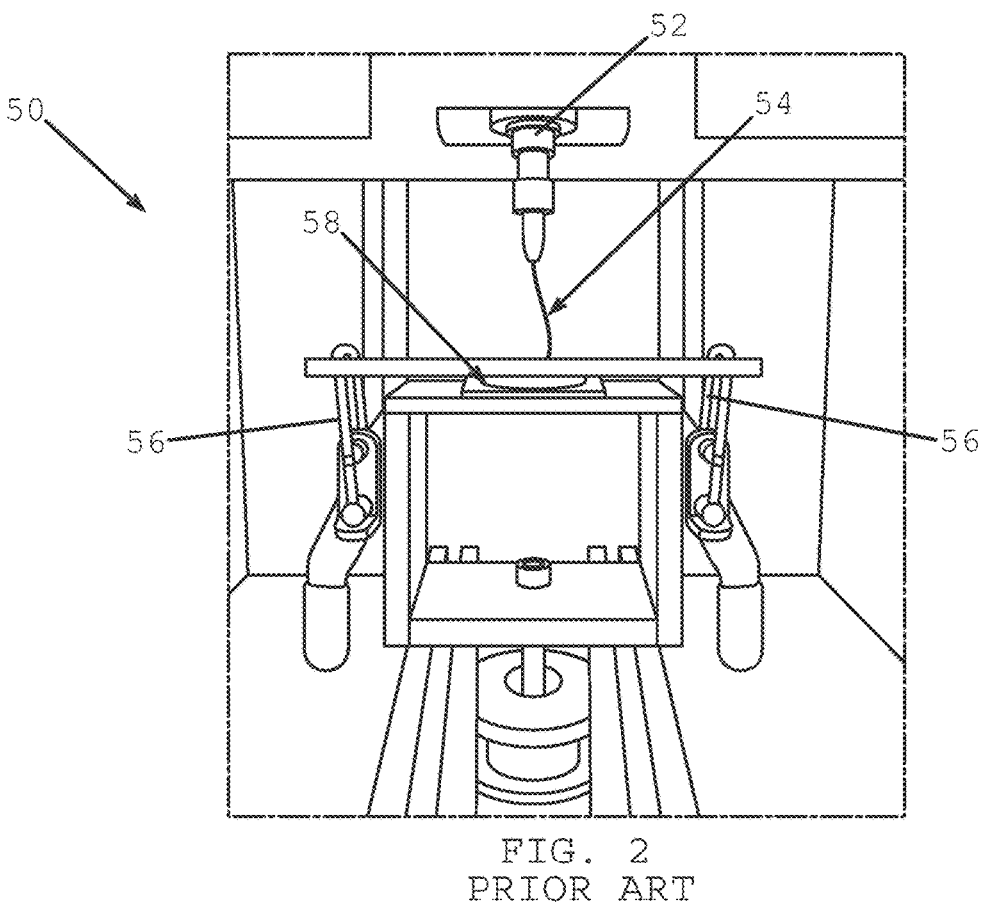
FIG. 2 is a perspective view a prior art system used for testing a needle stop.
Figure 3:
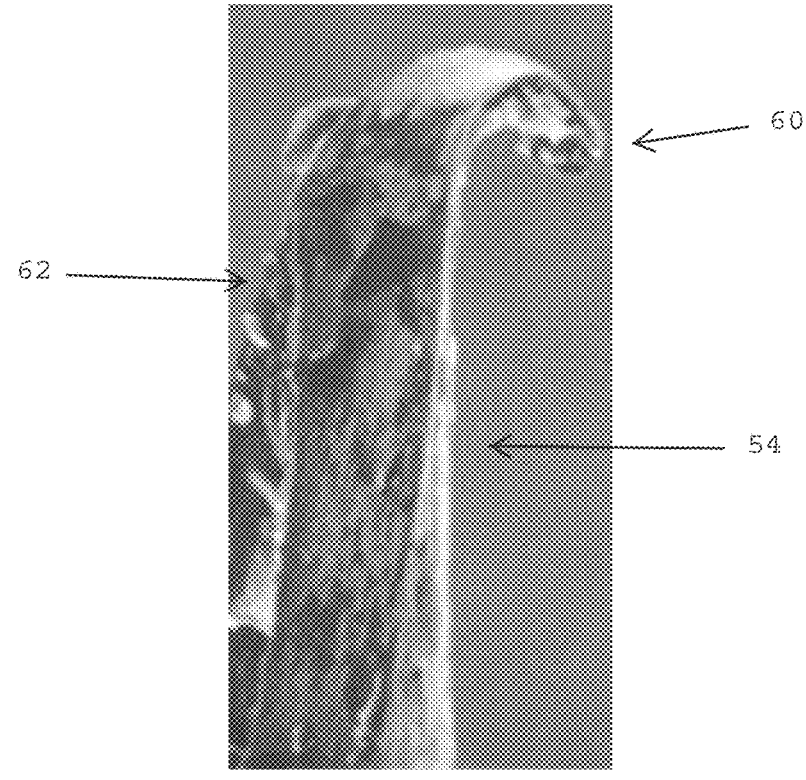
FIG. 3 is a perspective view of a prior art needle that is damaged and that has a bent needle tip.
Figure 4:
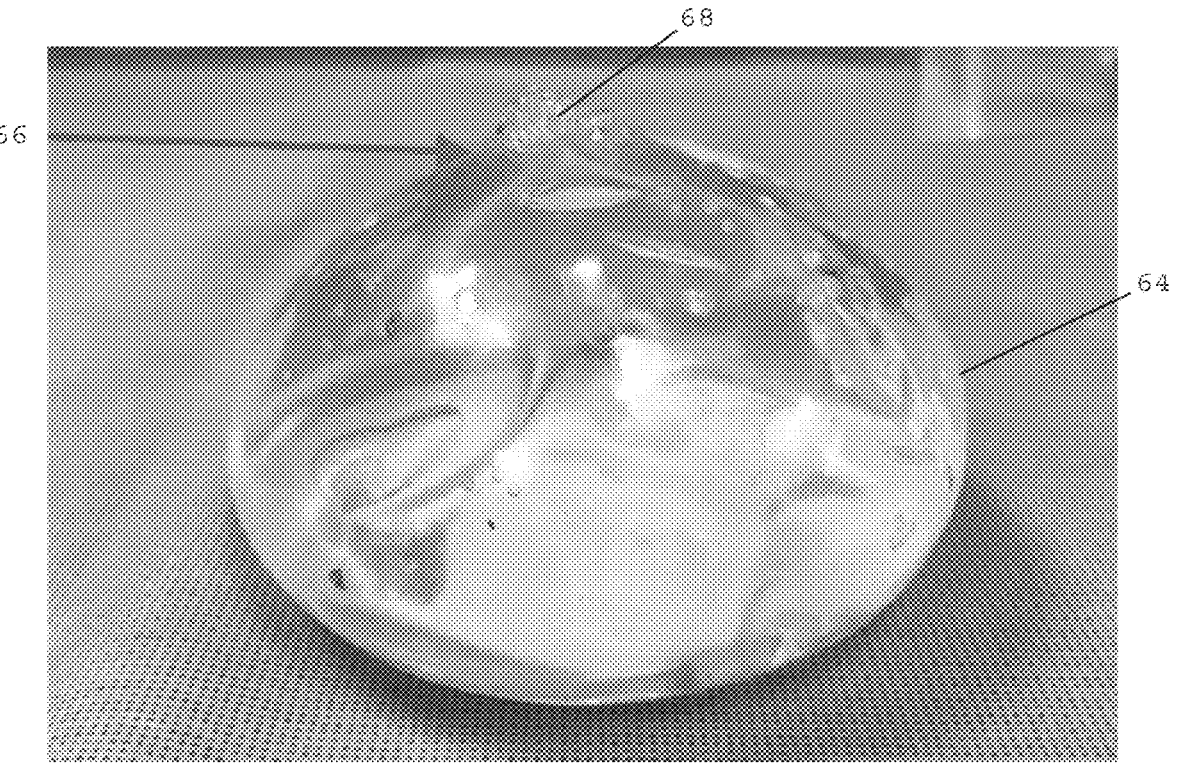
FIG. 4 is a perspective view of a prior art prosthetic implant having an outer shell with a puncture and filling material leaking through the puncture.
Figure 5:
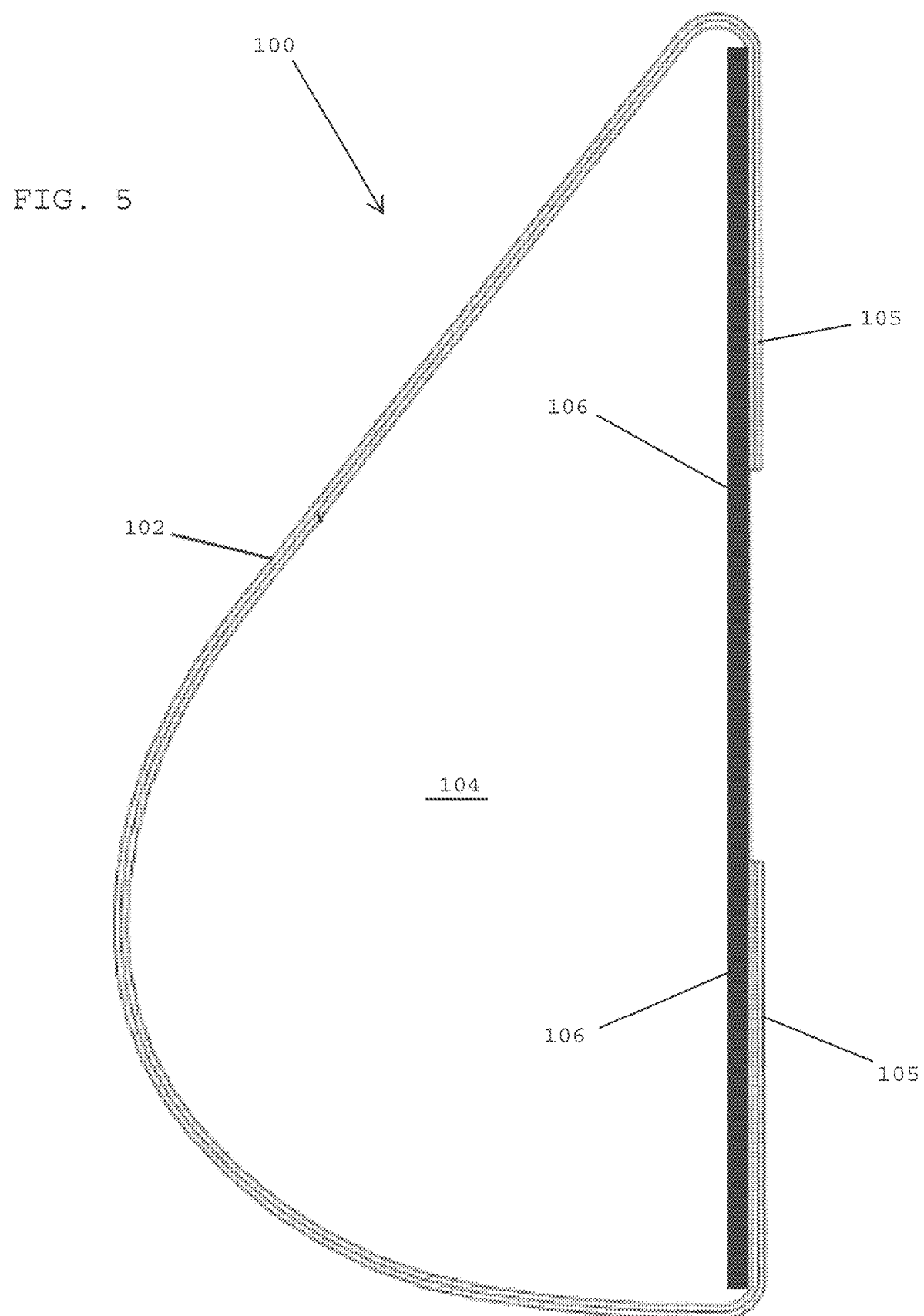
FIG. 5 is a cross-sectional view of a prosthetic implant have a self-sealing shell and a needle stop patch covering a posterior wall of the seal-sealing shell, in accordance with one embodiment of the present patent application.

Referring to FIG. 5, in one embodiment, a prosthetic implant 100 (e.g., a tissue expander) preferably includes a shell 102 (e.g., a silicone shell) having an interior chamber 104 that may be filled with a fluid such as saline to expand the size of the shell. In one embodiment, the shell 102 may be made of a self-sealing membrane such as the self-sealing membranes disclosed in commonly assigned U.S. Provisional Application No. 63/157,285, filed on Mar. 5, 2021, the disclosure of which is hereby incorporated by reference herein. In one embodiment, the shell 102 preferably has a posterior wall 105 that is covered by a needle stop patch 106 comprising one or more layers of a textile material, also referred to herein as textile layers.

Figure 6:
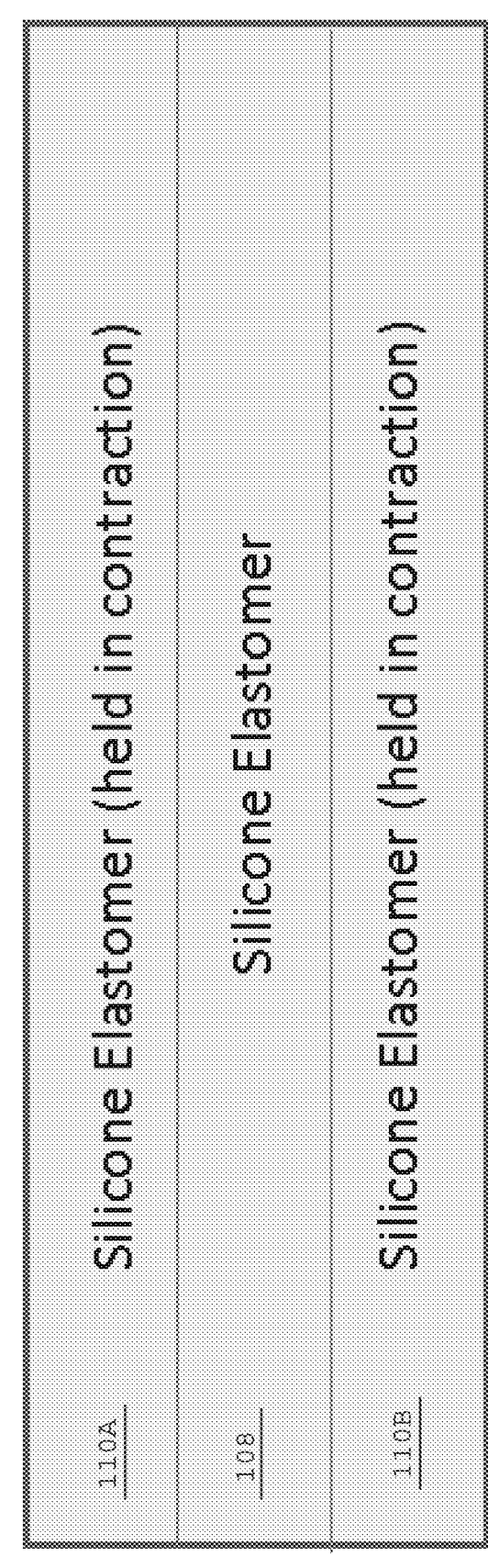
FIG. 6 is a schematic cross-sectional view of the self-sealing shell of the prosthetic implant shown in FIG. 5, in accordance with one embodiment of the present patent application.

Referring to FIG. 6, in one embodiment, the self-sealing shell membrane 102 (FIG. 5), such as the self-sealing membranes disclosed in commonly assigned U.S. Provisional Application No. 63/157,285, filed on Mar. 5, 2021, the disclosure of which is hereby incorporated by reference herein, may have three layers including an intermediate layer 108 of a silicone elastomer, and first and second outer layers 110A, 110B of a silicone elastomer that are held in contraction by the intermediate layer 108.

Figure 7:
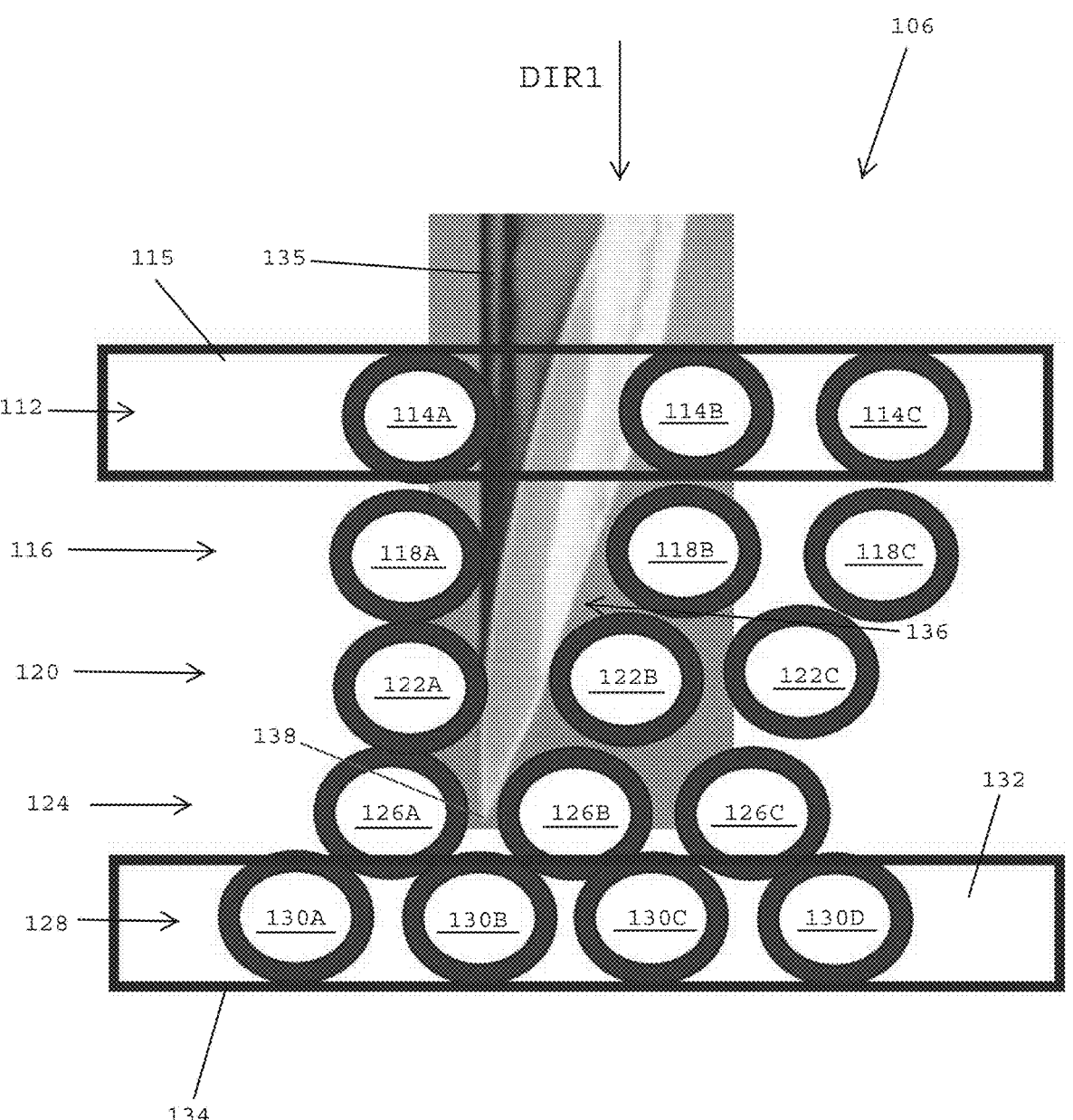
FIG. 7 is a schematic cross-sectional view of the needle stop patch shown in FIG. 5, in accordance with one embodiment of the present patent application.

Referring to FIG. 7, in one embodiment, the needle stop patch 106 (FIG. 5) preferably includes one or more layers of textile material. In one embodiment, the needle stop patch 106 preferably includes one or more layers of textile material that are joined together to form the needle stop patch. In one embodiment, the needle stop patch 106 preferably includes a first textile layer 112 including interwoven threads 114A-114C. The first textile layer 112 may be laminated or imbedded in a first layer 115 of a polymeric material.

In one embodiment, the needle stop patch 106 desirably includes a second textile layer 116 including a plurality of interwoven threads 118A-118C that are free to move relative to one another.

In one embodiment, the needle stop patch 106 preferably includes a third textile layer 120 having a plurality of interwoven threads 122A-122C that are free to move relative to one another.

In one embodiment, the needle stop patch 106 preferably includes a fourth textile layer 124 having a plurality of interwoven threads 126A-126C that are free to move relative to one another.

In one embodiment, the second, third and fourth textile layers 116, 120, and 124 are not laminated and/or embedded within a polymeric layer.

In one embodiment, the needle stop patch 106 preferably includes a fifth textile layer 128 having a plurality of interwoven threads 130A-130D that are laminated and/or embedded within a layer 132 of a polymeric material.

In one embodiment, the needle stop patch 106 is preferably positioned over a posterior wall of a shell of a prosthetic implant. In one embodiment, a bottom surface 134 of the fifth layer 128 of the needle stop patch 106 is preferably secured to an inner surface of a posterior wall of a shell of a prosthetic implant.

Referring to FIGS. 5 and 7, in one embodiment, a needle 135 having a tapered distal end 136 with a sharpened needle tip 138 may be inserted through the shell 102 of the prosthetic implant 100 for filling the implant shell. If the sharpened needle tip 138 is advanced too far toward the posterior wall 105 of the shell 102, the sharpened needle tip 138 may contact the needle stop patch 106.

Referring to FIG. 7, in one embodiment, the multiple textile layer construction of the needle stop patch 106 preferably engages the tapered distal end 136 of the needle 135 to apply frictional forces on the side of the needle as the needle advances in the direction DIR1. The multiple textile layers 112, 116, 120, 124, and 128 preferably have a specific denier and thread weave or geometries that "catch" the tapered distal end 136 and the needle tip 138 such that force is not overly localized on the needle tip. In one embodiment, each individual textile layer 112, 116,120, 124, and 128 of the needle stop patch 106 is not impenetrable on its own, however, the cumulative effect of the multiple textile layer construction desirably provides enough resistance to prevent the needle from completely passing through the needle stop patch 106 and/or piercing through the bottom surface 134 of the fifth textile layer 128 of the needle stop patch 106.

As used herein, Denier is a unit of linear mass density based on the length and weight of a thread or fiber. A single strand of silk is considered 1 denier, or more specifically, a 9,000 meter long strand of silk is about 1 gram. For a given material, the higher the denier count, the greater the diameter of the thread or fiber. Or for a given diameter, the higher the denier count, the greater the density of the thread or fiber In one embodiment, the denier count of the five layers 112, 116, 120, 124, and 128 may increase between the first layer 112 and the fifth layer 128 to progressively increase the resistance level for a needle passing through the needle stop patch 106.

Figure 8:
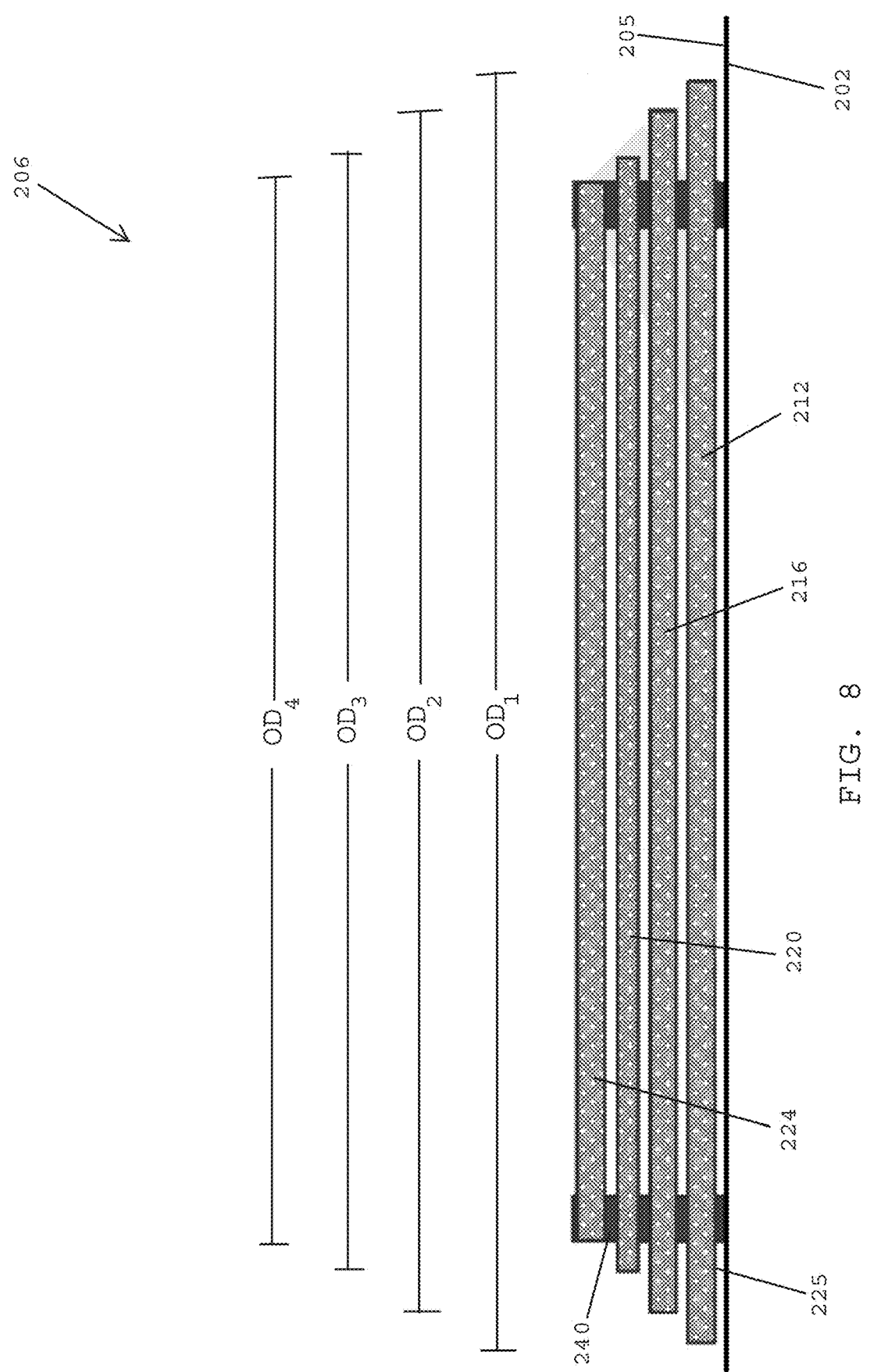
FIG. 8 is a cross-sectional view of a needle stop patch that covers a posterior wall of a shell of a prosthetic implant, in accordance with one embodiment of the present patent application.

Referring to FIG. 8, in one embodiment, a needle stop patch 206 preferably includes a plurality of textile layers 212, 216, 220, and 224. In one embodiment, the textile layers 212, 216, 220, and 224 have respective outer peripheral edges that define different outer diameters. In one embodiment, the outer peripheral edges of the textile layers are feathered, or progressively tapered, relative to one another to reduce a step affect and promote a gradual stiffness gradient between the respective textile layers 212, 216, 220, and 224. In one embodiment, the first textile layer 212 has outer diameter OD$_1$ that is greater than the outer diameter OD$_2$ of the second textile layer 216. In turn, the second textile layer 216 has the second outer diameter OD$_2$ that is greater than the third outer diameter OD$_3$ of the third textile layer 220. In turn, the third textile layer 220 has the third outer diameter OD$_3$ that is greater than the fourth outer diameter OD$_4$ of the fourth textile layer 224.

In one embodiment, the four textile layers 212, 216, 220, and 224 are joined together. In one embodiment, the four textile layers 212, 216, 220, and 224 are joined together at the respective outer peripheral edges thereof via a bonding material 240 that extends through the different textile layers. In one embodiment, the bonding material 240 may have a ring shape that extends adjacent the outer perimeter of the needle stop patch 206. In one embodiment, central regions of the textile layers 212, 216, 220, and 224 are not joined together, which preferably increases the flexibility of the needle stop patch 206 and minimizes the stiffness of the needle stop patch.

In one embodiment, the needle stop patch 206 may be secured to a wall of a shell of a prosthetic implant. In one embodiment, the needle stop patch 206 may be secured to an inner surface of a posterior wall 205 of a shell 202. In one embodiment, the bottom surface 225 of the fourth textile layer 224 is secured to the inner surface of the posterior wall 215 of the shell 202. In one embodiment, the bonding material 240 may be used for securing the needle stop patch 206 to a shell wall.

Figure 10A:
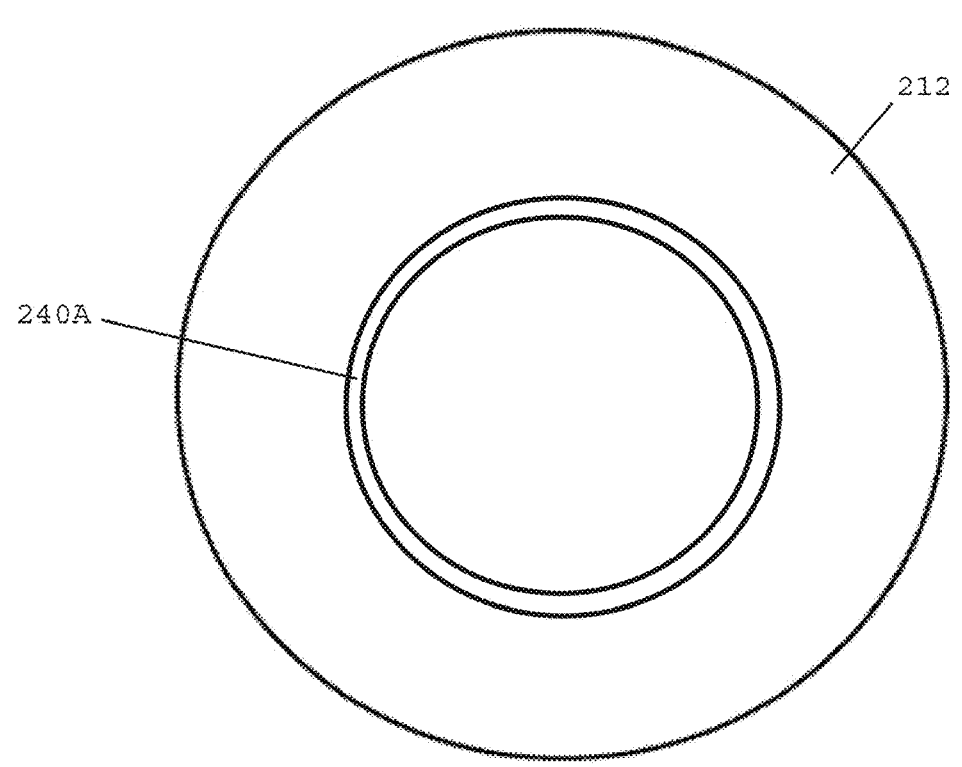
FIG. 10A is a top view of the assembly shown in FIG. 9A.

Referring to FIGS. 9A and 10A, in one embodiment, a first layer 212 of a needle stop patch 206 preferably has a top surface and the bottom surface 225. A first ring 240A of a bonding material may be assembled with the first textile layer 212. The first ring 240A of bonding material may be centered on the first textile layer 212

Figure 10B:
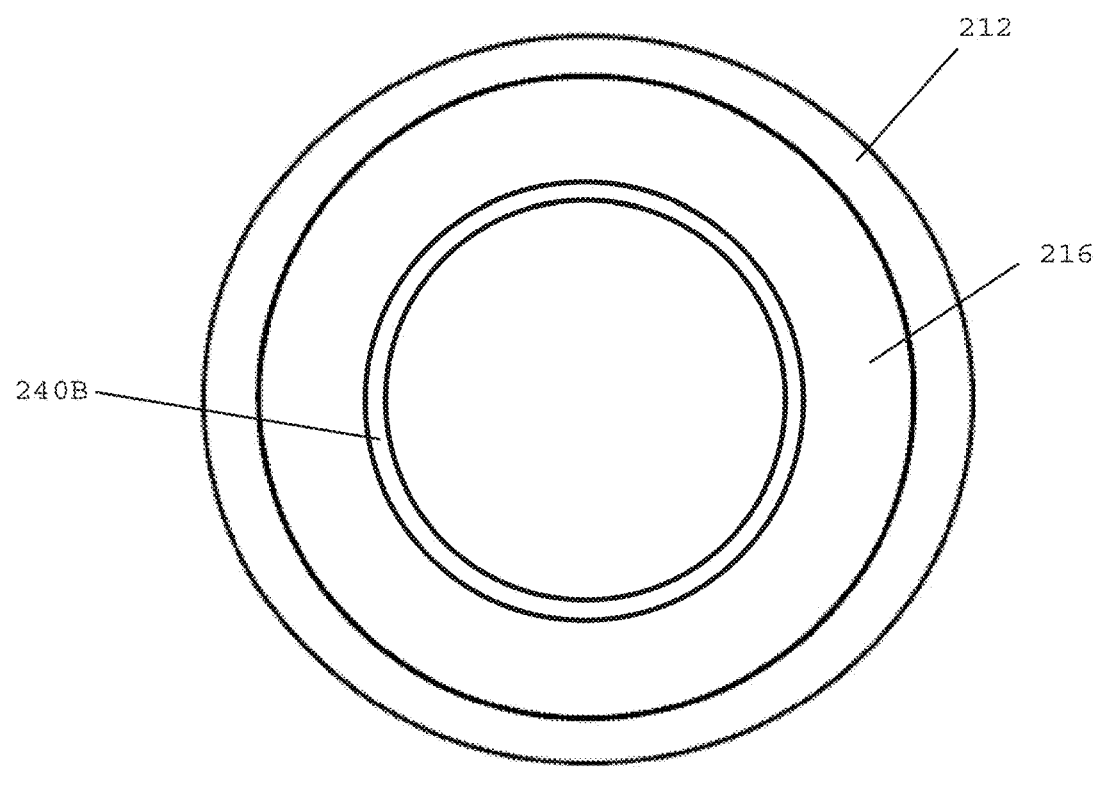
FIG. 10B is a top view of the assembly shown in FIG. 9B.

Referring to FIGS. 9B and 10B, in one embodiment, the second textile layer 216 is positioned atop the first ring 240A of the bonding material, which extends between a bottom surface of the second textile layer 216 and the top surface of the first textile layer 212. The second textile layer 216 may be centered over the first textile layer 212. The area of the first textile layer 212 is preferably greater than the area of the second textile layer 216.

Referring to FIGS. 9B and 10B, in one embodiment, a second ring 240B of a bonding material may be positioned atop the top surface of the second textile layer 216.

Figure 10C:
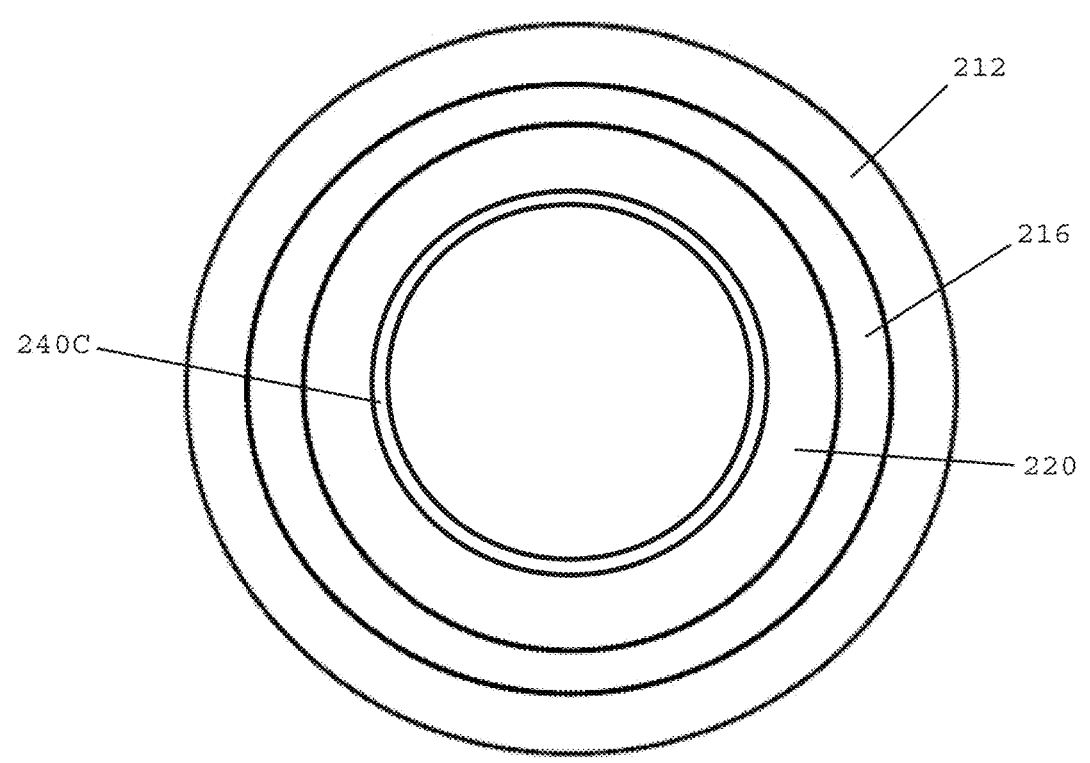
FIG. 10C is a top view of the assembly shown in FIG. 9C.

Referring to FIGS. 9C and 10C, in one embodiment, the third layer 220 of the textile material may be positioned atop the second ring 240B of bonding material that extends between a bottom surface of the third textile layer 220 and a top surface of the second textile layer 216. The third textile layer 220 may be centered over the second textile layer 216. The area of the second textile layer 216 is preferably greater than the area of the third textile layer 220.

Referring to FIGS. 9C and 10C, in one embodiment, a third ring 240C of a bonding material is positioned over the top surface of the third textile layer 220.

Figure 10D:
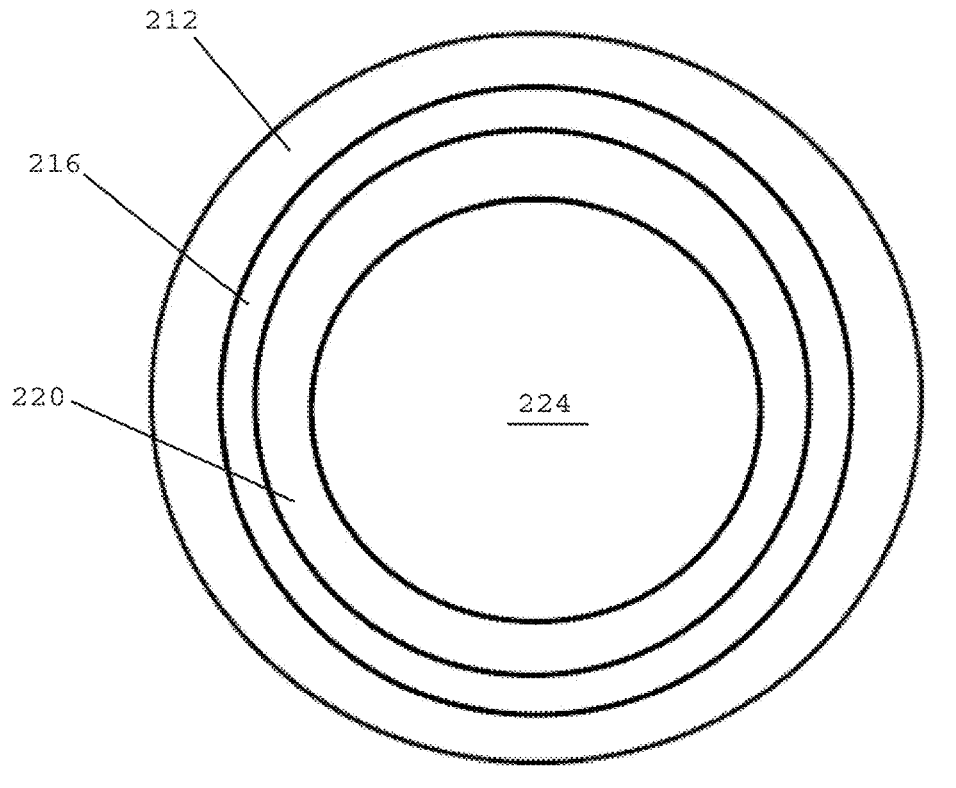
FIG. 10D is a top view of the assembly shown in FIG. 9A.

Referring to FIGS. 9D and 10D, in one embodiment, the fourth textile layer 224 is positioned atop the third ring 240C of bonding material that extends between a bottom surface of the fourth textile layer 224 and a top surface of the third textile layer 220. The fourth textile layer 224 may be centered over the third textile layer 220. The area of the third textile layer 220 is preferably greater than the area of the fourth textile layer 224.

In one embodiment, the rings 240A, 240B and 240C of the bonding material preferably have the same respective outer diameters and are preferably aligned with one another for joining the four textile layers 212, 216, 220, and 224 of the needle stop patch 206.

In one embodiment, the respective outer peripheries of the four textile layers may be compressed so that the bonding material within the bonding material rings 240A, 240B, 240C flows through the woven threads of the respective textile layers for bonding the textile layers together adjacent the outer peripheries thereof. As noted above, in one embodiment, only the outer peripheries of the four textile layers 212, 216, 220, and 224 are bonded together via the rings 240A-240C of the bonding material to enhance flexibility and/or reduce the overall stiffness of the needle stop patch 206. The flexibility of the needle stop patch 206 preferably enables the patch and the shell that contains the patch to be folded during insertion into a patient.

Figure 11:
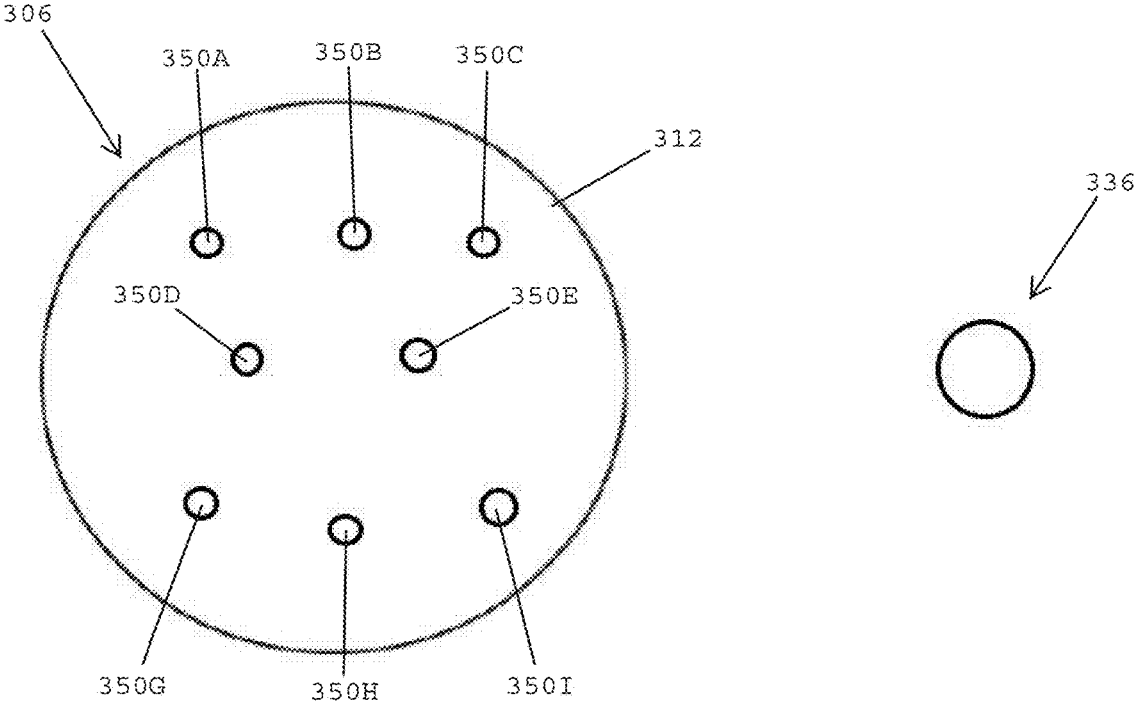
FIG. 11 shows a top view of a first textile layer of a needle stop patch and a cross-sectional view of a needle, in accordance with one embodiment of the present patent application.

Referring to FIG. 11, in one embodiment, a needle stop patch 306 preferably includes a textile layer 312 having a plurality of spaced holes 350A-350I extending therethrough. In one embodiment, the holes 350A-350I preferably enable fluid to communicate with an inner lumen of the shell when a filling needle bottoms out on the needle stop patch 306, even in instances where a textile layer may occlude a hole.

In one embodiment, each hole 350A-350I of the textile layer 312 desirably has an inner diameter ID$_1$ of about 0.1 mm to 3 mm. In one embodiment, the sum of the areas of the holes 350A-350I is preferably greater than the outer diameter OD$_5$ of a filling needle 336 that may engage the textile layer 312 to prevent any bottlenecks and/or fluid accumulation within the needle stop patch 306. Designing a needle stop patch 306 so that the sum of the areas of the holes 350A-350I formed in the textile layer 312 is greater than the outer diameter OD$_5$ of the needle 336, preferably avoids fluid accumulation within the one or more textile layers, which prevents localized accumulation of fluid within the needle stop patch. In one embodiment, the holes between the fibers naturally form as part of the woven, nonwoven, knit and other patterns in summation act as the fluid channels. In one embodiment, holes are further created through the textile via additional cutting or punching processes.

Figure 12:
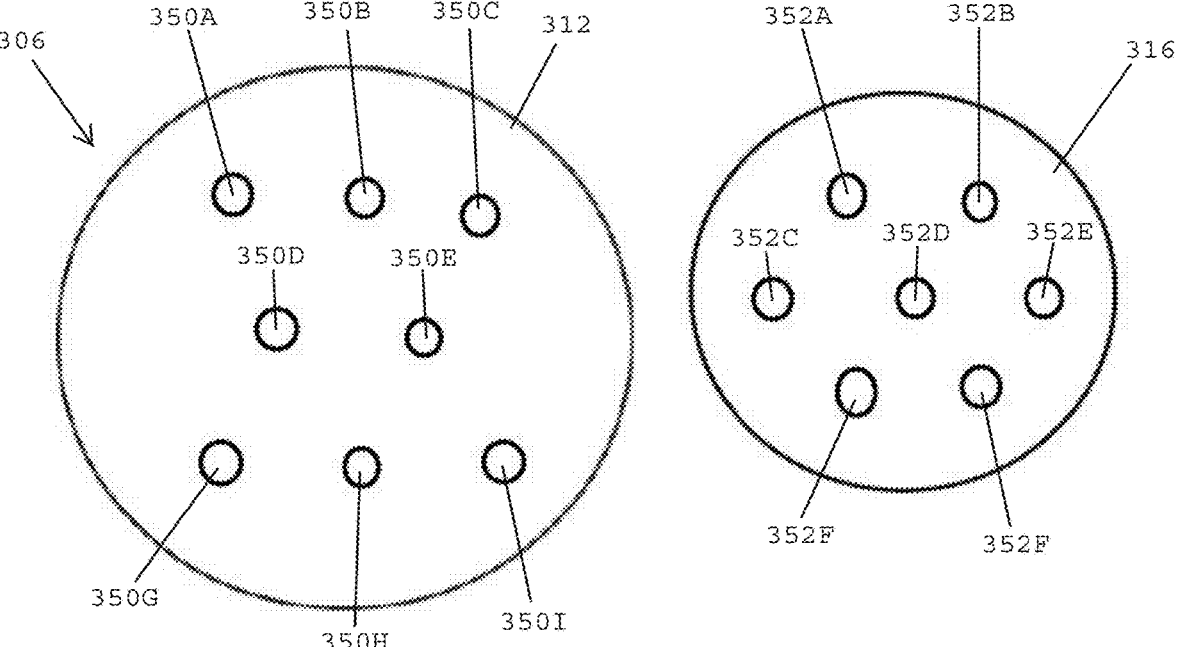
FIG. 12 shows a top view of the first textile layer of FIG. 11 and a second textile layer that is assembled with the first textile layer to make a needle stop patch, in accordance with one embodiment of the present patent application.

Referring to FIG. 12, in one embodiment, the needle stop patch 306 preferably includes the first textile layer 312 having holes 350A-350I and a second textile layer 316 that may be joined with the first textile layer 312 using a methodology that is like that shown and described above in FIGS. 9A-9D and 10A-10D. In one embodiment, the second textile layer 316 preferably includes holes 352A-352I extending therethrough. The holes 352A-352I of the second textile layer 316 are preferably offset from the holes 350A-350I of the first textile layer 312 so that the holes in the respective layers do not line up with one another when the first and second textile layers 312, 316 are assembled with one another.

Figure 13:
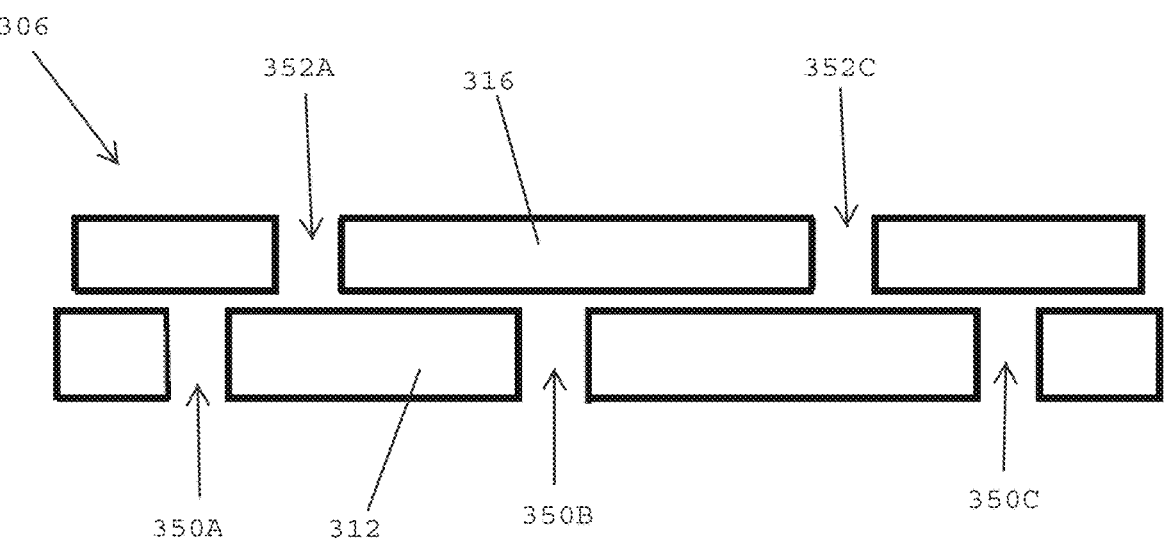
FIG. 13 is a cross-sectional view of the first and second textile layers of FIG. 12 after the second textile layer has been assembled over the first textile layer.

FIG. 13 shows the first and second textile layers 312, 316 assembled with one another. In one embodiment, the holes 350A, 350C of the first textile layer 312 are not in alignment with the holes 352A, 352C on the second textile layer 316. In FIG. 13 only central regions of the first and second textile layers 312, 316 are shown so that the outer peripheries of the first and second textile layers are not shown. In FIG. 13, all the holes shown in the first and second layers in FIG. 12 are not shown in FIG. 13. FIG. 13 merely provides an example of how the holes and the respective layers 312, 316 are not in alignment with one another.

Figure 14:
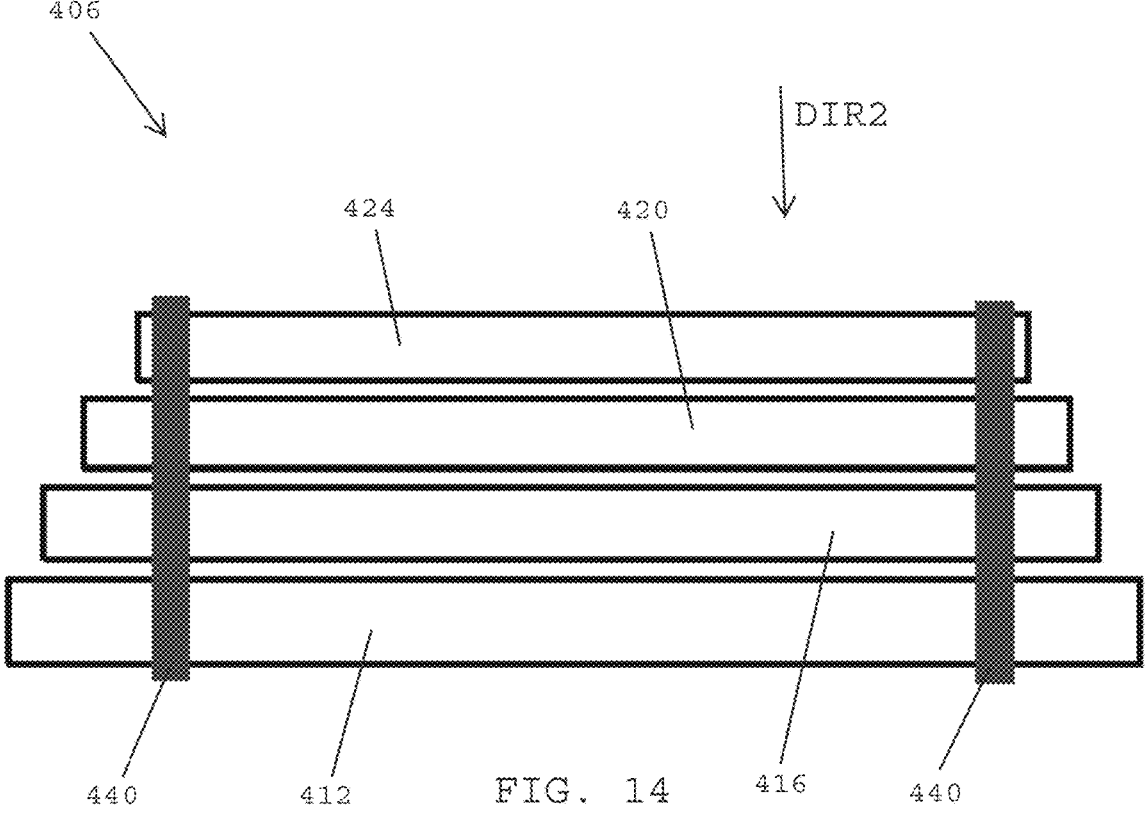
FIG. 14 is a cross-sectional view of a needle stop patch for a shell of a prosthetic implant, in accordance with one embodiment of the present patent application.

Referring to FIG. 14, in one embodiment, a needle stop patch 406 preferably has a plurality of textile layers whereby the textile denier/weave and polymeric material durometer may progressively increase for each layer to provide a progressive stopping effect on a needle tip that is passed through the needle stop patch 406. In one embodiment, a top layer 324 has a durometer that is lower than a first intermediate layer 320. In turn, the first intermediate layer 320 has a lower durometer than a second intermediate layer 316. In turn, the second intermediate layer 316 has a lower durometer than the bottom layer 312. Thus, the durometers of the respective layers 324, 320, 316, and 312 progressively increase for each successive layer from the top layer 424 to the bottom layer 412 to provide a progressive stopping effect on a needle tip that engages and/or passes through the needle stop patch 406 in the direction indicated DIR2.

In one embodiment, the respective layers 424, 420, 416, and 412 preferably have different outer diameters so that the final assembly has feathered edges that are designed to reduce any step effects, thereby promoting gradual stiffness gradients.

In one embodiment, a bonding material 440 may be used for bonding the layers 424, 420, 416, and 412 together. In one embodiment, the bonding material 440 preferably bonds only the outer peripheries of the respective layers to enhance flexibility and reduce the overall stiffness of the needle stop patch 406.

In one embodiment, adding additional textile layers to a needle stop patch may increase the needle penetration resistance that is provided by a needle stop patch. For example, a needle stop patch having five textile layers may provide more penetration resistance than a needle stop patch having four textile layers.

Figure 15:
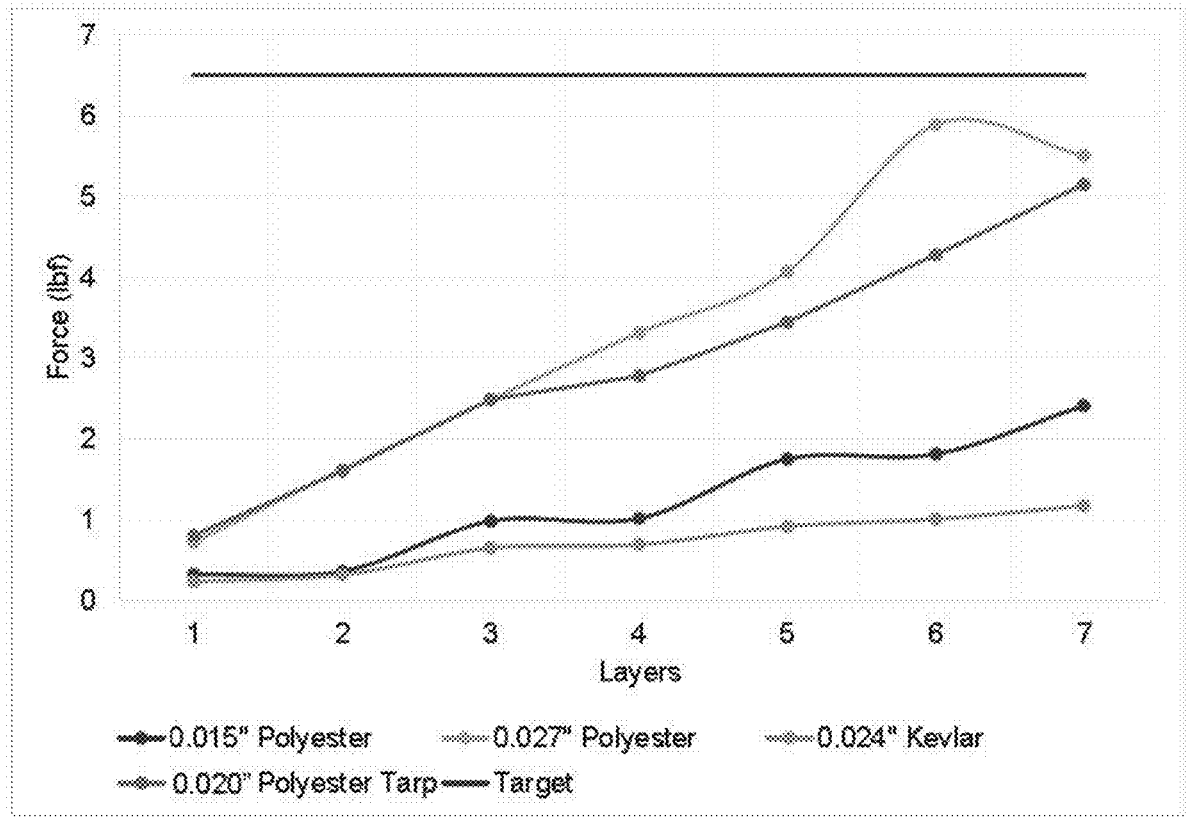
FIG. 15 is a graph of the force required to penetrate needle stop patches made of different materials and having a different number of layers to show the penetration resistance of the different needle stop patches.

FIG. 15 is a graph which shows the increasing penetration resistance as additional textile layers are added to a needle stop patch. The graph plots different types of textile layers and how the penetration resistance is increased by adding additional layers to a needle stop patch.

Figure 16:
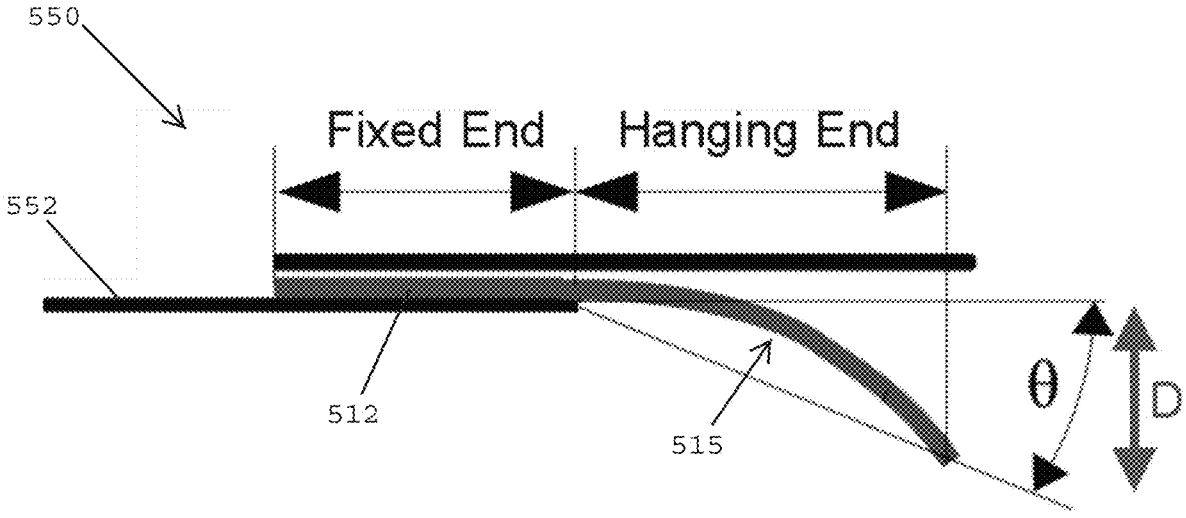
FIG. 16 shows a prior art method of testing the stiffness of a textile material to determine its suitability for use in a needle stop patch, in accordance with one embodiment of the present patent application.

In one embodiment, it may be desirable to maximize the flexibility of a needle stop patch by increasing the flexibility of the textile layers that are used to make a needle stop patch. Referring to FIG. 16, in one embodiment, a prior art testing system 550 may be utilized for evaluating the stiffness and/or flexibility of a textile layer. In one embodiment, the testing system 550 preferably includes a horizontally extending surface 552 that is adapted to support a fixed end of a textile layer 512. The textile layer 512 desirably includes a hanging end 515 that is not supported by the support surface 552 so that the hanging end 515 is free to flex downward into an unsupported, open space. In one embodiment, the fixed end of the textile layer 512 has a length of about 0.25 inches and the hanging end 515 of the textile layer 512 has a hanging length of about 2.75 inches. In one embodiment, the width of the textile layer 512 may be approximately two (2) inches.

Figure 17:
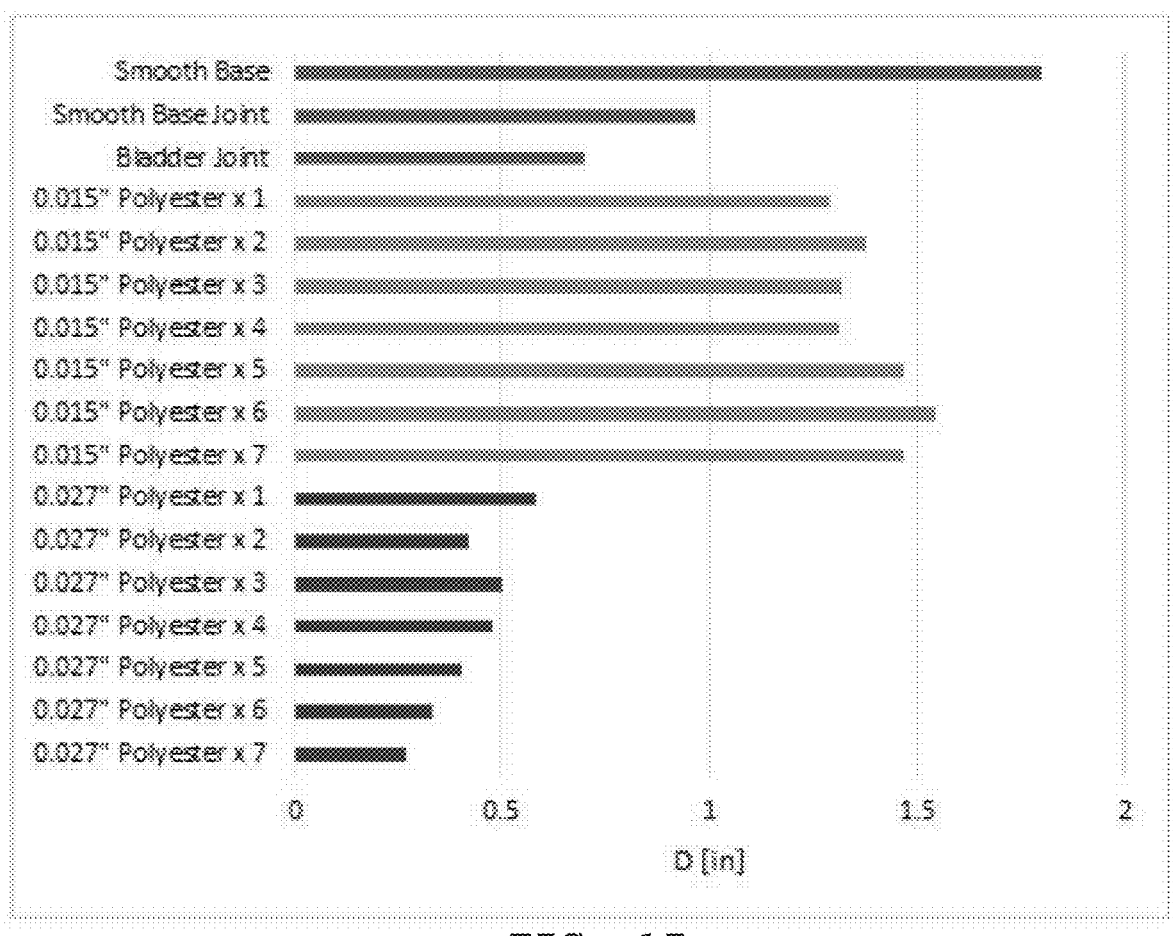
FIG. 17 is a graph that shows the flexibility of needle stop patches having different designs and how the flexibility changes in response to the number of textile layers added to a needle stop patch, in accordance with one embodiment of the present patent application.

In one embodiment, it is desirable to increase penetration resistance fora needle stop patch with no significant loss of flexibility for the needle stop patch. FIG. 17 is a graph that shows that different materials may be selected to maximize resistance to penetration while providing no significant loss of flexibility. In FIG. 17, a needle stop patch including textile layers made of 0.015-inch polyester are significantly more flexible than a needle stop patch including textile layers made of 0.027-inch polyester.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A prosthetic implant comprising:
   a silicone shell having an anterior wall and a posterior wall;
   a needle stop patch secured over an inner surface of said posterior wall of said silicone shell;
   said needle stop patch including two or more layers of a textile material that are stacked atop one another; and
   a bonding material for bonding together said two or more layers of said textile material that are stacked atop one another,
   wherein each of said two or more layers of said textile material has a circular or oval shape.

2. The prosthetic implant as claimed in claim 1, wherein said textile material comprises woven threads or woven fibers.

3. The prosthetic implant as claimed in claim 1, wherein said bonding material passes through said two or more layers of said textile material.

4. The prosthetic implant as claimed in claim 3, wherein each of said two or more layers has an outer edge that defines an outer perimeter.

5. The prosthetic implant as claimed in claim 4, wherein only the outer perimeters of each of said two or more layers are bonded together.

6. The prosthetic implant as claimed in claim 4, wherein the outer perimeter of a top layer of said two or more layers defines a first area and the outer perimeter of a bottom layer of said two or more layers defines a second area that is larger than the first area of said top layer, and wherein the outer perimeter of an intermediate layer of said two or more layers that is between said top layer and said bottom layer defines an intermediate area that is larger than the first area and smaller than the second area.

7. The prosthetic implant as claimed in claim 6, wherein the respective outer edges of said two or more layers are feathered for minimizing step effects between adjacent ones of said two or more layers.

8. The prosthetic implant as claimed in claim 1, wherein said bonding material secures said needle stop patch to said posterior wall of said silicone shell.

9. The prosthetic implant as claimed in claim 1, wherein said bonding material has a ring shape that matches the circular or oval shape of each of said two or more layers of said textile material.

10. The prosthetic implant as claimed in claim 1, wherein each of said two or more layers of said textile material is laminated in elastomeric sheeting to form two or more elastomeric layers.

11. The prosthetic implant as claimed in claim 1, wherein said anterior wall of said silicone shell comprises a self-sealing membrane, wherein said self-sealing membrane has a three-layer construction comprising:

a middle layer of an elastomeric material having first and second major surfaces;

a first outer layer of an elastomeric material overlying the first major surface of said middle layer; and a second outer layer of an elastomeric material overlying the second major surface of said middle layer, wherein said middle layer of said elastomeric material holds said first and second outer layers of said elastomeric material in contraction.

12. The prosthetic implant as claimed in claim 1, wherein each said layer of said two or more layers of said textile material has a top surface, a bottom surface and a plurality of holes that extend from the top surface to the bottom surface, said prosthetic implant further comprising a needle for filling said silicone shell with a fluid, said needle having a cross-sectional area, wherein a total combined area of said plurality of said holes for each said layer is greater than the cross-sectional area of said needle.

13. The prosthetic implant as claimed in claim 1, wherein a denier count of said two or more layers progressively increases from a top layer to a bottom layer of said needle stop patch for providing said needle stop patch with a progressively increasing resistance level from said top layer to said bottom layer.

14. A prosthetic implant comprising:

a silicone shell having an anterior wall and a posterior wall;

a needle stop patch secured over an inner surface of said posterior wall of said silicone shell;

said needle stop patch including a plurality of layers of a textile material that are stacked atop one another; and a bonding material for joining together said plurality of layers of said textile material that are stacked atop of another, wherein each of said two or more layers of said textile material has a circular or oval shape, and wherein said bonding material has a ring shape that matches the circular or oval shape of each of said two or more layers of said textile material.

15. The prosthetic implant as claimed in claim 14, further comprising a self-sealing membrane integrated into said anterior wall of said silicone shell.

16. The prosthetic implant as claimed in claim 15, wherein said self-sealing membrane comprises:

a middle layer of an elastomeric material having first and second major surfaces;

a first outer layer of an elastomeric material overlying the first major surface of said middle layer; and a second outer layer of an elastomeric material overlying the second major surface of said middle layer, wherein said middle layer of said elastomeric material holds said first and second outer layers of said elastomeric material in contraction, and wherein an outer surface of said first outer layer of said elastomeric material is secured to an inner surface of said anterior wall of said silicone shell.

17. The prosthetic implant as claimed in claim 14, wherein said plurality of layers of the textile material that are stacked atop one another comprises:

a top layer having an outer edge defining a first area;

a bottom layer having an outer edge defining a second area that is larger than the first area of said top layer; and an intermediate layer disposed between said top layer and said bottom layer having an outer edge that defines an intermediate area that is larger than the first area of said top layer and smaller than the second area of said bottom layer.

18. The prosthetic implant as claimed in claim 17, wherein the respective outer edges of each of said plurality of layers are feathered for minimizing step effects between adjacent ones of said plurality of layers.

19. The prosthetic implant as claimed in claim 14, wherein each said layer of said plurality of layers of said textile material has a top surface, a bottom surface and a plurality of holes that extend from the top surface to the bottom surface, further comprising a needle for filling said silicone shell with a fluid, said needle having a cross-sectional area, wherein a total combined area of said plurality of holes for each said layer is greater than the cross-sectional area of said needle.

20. The prosthetic implant as claimed in claim 17, wherein a denier count of each said layer progressively increases from said top layer to said bottom layer for progressively increasing resistance levels within said needle stop patch.

21. A method of making a multi-layer needle stop patch for a silicone shell comprising:

obtaining a first layer of a textile material, wherein said first layer has an outer edge that defines a first area for said first layer;

centering a second layer of a textile material over said first layer, wherein said second layer is centered over said first layer and has an outer edge that defines a second area for said second layer that is less than the first area for said first layer;

centering a third layer of a textile material over said second layer, wherein said third layer is centered over said second layer and has an outer edge that defines a third area for said third layer that is less than the second area for said second layer;

centering a fourth layer of a textile material over said third layer, wherein said fourth layer is centered over said third layer and has an outer edge that defines a fourth area for said fourth layer that is less than the third area for said third layer; and bonding said respective outer edges of said first, second, third and fourth layers together.

22. The method as claimed in claim 21, wherein the respective outer edges of said layers are feathered for reducing step effects between said first, second, third and fourth layers.

23. The method as claimed in claim 21, further comprising:

providing a silicone shell having an anterior wall and a posterior wall; and securing said first layer of said multi-layer needle guard to an inner surface of said posterior wall of said silicone shell.

* * * * *